US00PP12293P2

(12) United States Plant Patent
Koppe

(10) Patent No.: US PP12,293 P2
(45) Date of Patent: Dec. 18, 2001

(54) BEGONIA PLANT NAMED 'BACCHUS'

(75) Inventor: Lubbertus H. Koppe, Ermelo (NL)

(73) Assignee: Koppe Veredeling B.V., Ermelo (NL)

( * ) Notice: Subject to any disclaimer, the term of this patent is extended or adjusted under 35 U.S.C. 154(b) by 0 days.

(21) Appl. No.: 09/320,926

(22) Filed: May 27, 1999

(51) Int. Cl.[7] ..... A01H 5/00

(52) U.S. Cl. ..... Plt./349

(58) Field of Search ..... Plt./349

(56) References Cited

PUBLICATIONS

UPOV–ROM GTITM Computer Database 2000/2, GTI Jouve Retrieval Software, Citations for Begonia plant named 'Bacchus', 2000.*

* cited by examiner

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Begonia plant named 'Bacchus', characterized by its compact and freely branching plant habit; fully double intense red flowers that are about 6 to 8 cm in diameter; short peduncles and short pedicels; and excellent postproduction longevity.

1 Drawing Sheet

BACKGROUND OF THE INVENTION

The present invention relates to a new and distinct cultivar of Begonia plant, botanically known as *Begonia×hiemalis*, commercially known as Elatior Begonia, and hereinafter referred to by the name 'Bacchus'.

The new Begonia was discovered by the Inventor in a controlled environment in Ermelo, The Netherlands, in December, 1994, as a naturally-occurring mutation of *Begonia×hiemalis* 'Barkos', disclosed in U.S. Plant Pat. No. 9,523. The new Begonia was observed as a single plant in a group of flowering plants of the parent cultivar. The selection of this plant was based on its unique flower color.

Asexual reproduction of the new Begonia by leaf and terminal cuttings taken in a controlled environment in Ermelo, The Netherlands, has shown that the unique features of this new Begonia are stable and reproduced true to type in successive generations.

SUMMARY OF THE INVENTION

The cultivar 'Bacchus' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Bacchus'. These characteristics in combination distinguish 'Bacchus' as a new and distinct Begonia:

1. Compact and freely branching plant habit.
2. Fully double intense red flowers that are about 6 to 8 cm in diameter.
3. Short peduncles and short pedicels.
4. Excellent postproduction longevity.

In side-by-side comparisons conducted by the Inventor in Ermelo, The Netherlands, plants of the new Begonia differ from plants of the parent cultivar Barkos in the following characteristics:

1. Plants of the new Begonia are more compact than plants of the cultivar Barkos.
2. Flowers of plants of the new Begonia are more intense red than flowers of plants of the cultivar Barkos.
3. Plants of the new Begonia have shorter peduncles and shorter pedicels than plants of the cultivar Barkos.
4. Flowers of plants of the new Begonia are longer-lasting than flowers of plants of the cultivar Barkos.

BRIEF DESCRIPTION OF THE PHOTOGRAPH

The accompanying colored photograph illustrates the overall appearance of the new Begonia, showing the colors as true as it is reasonably possible to obtain in colored reproductions of this type. The photograph comprises a top perspective view of a typical flowering plant of 'Bacchus'. Flower and foliage colors in the photograph may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Ermelo, The Netherlands, under commercial practice in a glass-covered greenhouse. Average day and night temperatures were 20° C. during the first three to four weeks then lowered to an average day and night temperature of 19° C. until flowering. Four weeks after planting, one week of long nyctoperiods were given followed by short nyctoperiods of eight hours. Measurements and numerical values represent averages for typical flowering plants that were about 10 to 12 weeks old.

Botanical classification: *Begonia×hiemalis* cultivar Bacchus.

Commercial classification: Elatior Begonia.

Parentage: Naturally-occurring mutation of *Begonia×hiemalis* 'Barkos', disclosed in U.S. Plant Pat. No. 9,523.

Propagation:

*Type.*—Terminal cuttings.

*Time to develop roots.*—About 42 days with soil temperatures of 20° C.

*Rooting habit.*—Fine, fibrous, well-branched, and spreading; plants do not form tubers.

Plant description:

*Plant form.*—Compact; upright and somewhat spreading potted plant; freely branching with good stem and stem base strength. Flowers are fully double and abundant. Plants flower continuously.

*Growth habit.*—Moderate growth rate, vigorous. Suitable for 11 to 15-cm containers. Under optimal environmental and cultural conditions, usually 10 to 12 weeks are required to produce proportional 13-cm potted plants from terminal cuttings. Vegetative shoots are formed at basal nodes and flowering shoots are formed at upper nodes.

*Plant height.*—About 22 to 24 cm.

*Plant width.*—About 26 to 29 cm.

*Leaves.*—Arrangement: Simple, alternate. Length: About 11.5 cm. Width: About 11.5 cm. Shape: Asymmetrical, more or less reniform. Apex: Acuminate. Base: Cordate. Margin: Doubly serrate. Texture: Slightly pubescent. Petiole length: About 2 to 5 cm. Color: Young and fully expanded foliage, upper surface: 147A to 147B. Young and fully expanded foliage, lower surface: 147B to 147C. Venation, upper and lower surfaces: 144D to 146D with medium to strong purple anthocyanin coloration. Petiole: 144D with medium to strong anthocyanin coloration.

Flower description:

*Flowering habit.*—Large and fully double flowers with numerous tepals arranged in axillary cymes. Usually three to five flowers per cyme. Many cymes in flower simultaneously. Flowering continuous.

*Natural flowering season.*—Plants will flower year around regardless of nyctoperiod, however plants flower earlier and more abundantly from mid-February until November in the Northern Hemisphere.

*Flowers.*—Shape: Rounded. Diameter: About 7 cm. Depth (height): About 3 cm.

*Flower buds.*—Length: About 2 to 3 cm. Diameter: About 1.5 to 2 cm. Color: 46B to 46C.

*Tepals.*—Arrangement: Rosette. Shape: Very broadly cordate with rounded apex. Margin: Crenate. Quantity per flower: Usually about 35 per flower. Size: Outer tepals: Length: About 3 to 3.8 cm. Width: About 3.2 to 4 cm. Inner tepals: Length: About 1.5 to 2.5 cm. Width: About 1.5 to 2.5 cm. Texture: Smooth, satiny, glabrous. Color: When opening: 46B. Fully opened, upper surface: 46B. Fully opened, lower surface: 46C. Fading to: 46B.

*Peduncles.*—Angle: Erect to bent. Length: About 7 to 9 cm. Texture: Slightly pubescent. Color: 146D to 144D with slight to moderate purple anthocyanin coloration.

*Pedicels.*—Angle: Bent. Length: About 1.5 to 3 cm. Texture: Slightly pubescent. Color: Close to 179A.

*Bracts.*—Arrangement: Two, opposite. Shape: Very broadly cordate. Margin: Entire. Color: Upper surface: 46B. Lower surface: 47B to 47C.

*Reproductive organs.*—Stamens: None observed. Pistils: None observed.

Postproduction longevity:

*Individual flowers.*—Generally about 2 to 3 weeks on the plant.

*Whole plants.*—About 6 weeks under interior conditions.

Disease resistance: Resistance to diseases common to Begonia has not been determined.

Seed production: Seed production has not been observed as reproductive organs are not formed.

It is claimed:

1. A new and distinct cultivar of Begonia plant named 'Bacchus', as illustrated and described.

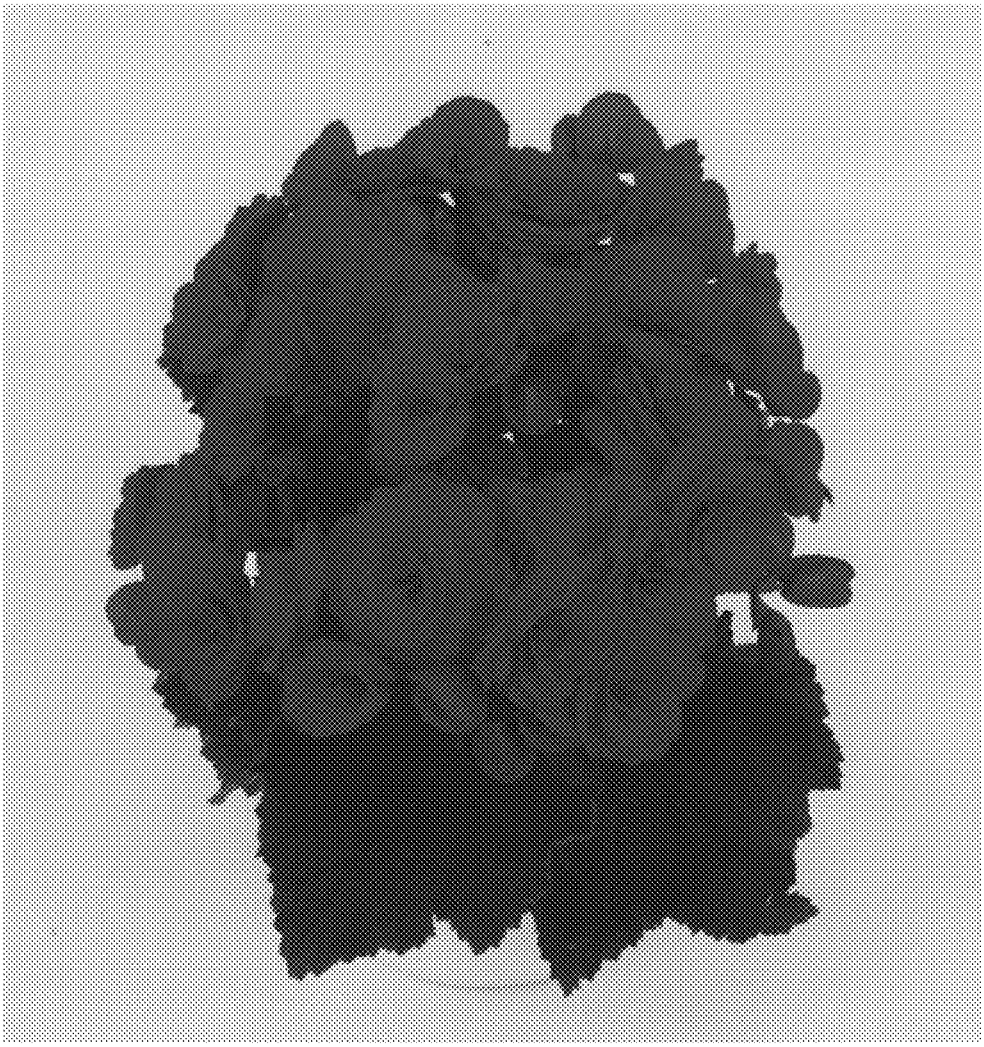

* * * * *